(12) United States Patent
Vaillant et al.

(10) Patent No.: US 10,022,101 B2
(45) Date of Patent: Jul. 17, 2018

(54) X-RAY/INTRAVASCULAR IMAGING COLOCATION METHOD AND SYSTEM

(71) Applicant: General Electric Company, Schenectady, NY (US)

(72) Inventors: Regis Vaillant, Buc (FR); Francisco Sureda, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 27 days.

(21) Appl. No.: 15/056,566

(22) Filed: Feb. 29, 2016

(65) Prior Publication Data

US 2017/0245822 A1 Aug. 31, 2017

(51) Int. Cl.
| | |
|---|---|
| G06K 9/00 | (2006.01) |
| A61B 6/00 | (2006.01) |
| A61B 5/0432 | (2006.01) |
| A61B 6/12 | (2006.01) |
| A61B 8/08 | (2006.01) |
| A61B 8/12 | (2006.01) |
| G06T 7/00 | (2017.01) |
| A61B 5/00 | (2006.01) |

(52) U.S. Cl.
CPC .......... *A61B 6/5235* (2013.01); *A61B 5/0071* (2013.01); *A61B 5/0084* (2013.01); *A61B 5/0432* (2013.01); *A61B 5/7289* (2013.01); *A61B 6/12* (2013.01); *A61B 6/461* (2013.01); *A61B 6/463* (2013.01); *A61B 6/481* (2013.01); *A61B 6/487* (2013.01); *A61B 6/503* (2013.01); *A61B 6/504* (2013.01); *A61B 6/5211* (2013.01); *A61B 6/5247* (2013.01); *A61B 6/5288* (2013.01); *A61B 8/0883* (2013.01); *A61B 8/0891* (2013.01); *A61B 8/12* (2013.01); *G06T 7/0012* (2013.01); *A61B 6/4441* (2013.01); *G06T 2207/10121* (2013.01); *G06T 2207/30101* (2013.01)

(58) Field of Classification Search
CPC .................... A61B 6/5235; G06T 2207/10121
See application file for complete search history.

(56) References Cited

U.S. PATENT DOCUMENTS

| | | | | |
|---|---|---|---|---|
| 2012/0300903 | A1* | 11/2012 | Yao | A61B 6/12 378/62 |
| 2014/0003688 | A1* | 1/2014 | Hansis | A61B 6/032 382/130 |
| 2017/0091927 | A1* | 3/2017 | Auvray | A61B 6/5235 |

* cited by examiner

*Primary Examiner* — Oneal R Mistry

(57) ABSTRACT

In the present invention, a method and associated system is provided that produces a new sequence of combined X-ray/fluoro images obtained in synchrony with intravascular dataset/images. This synchronization is based on the time tags recorded at the acquisition of one dataset of the X-ray/fluoroscopic images and the intravascular images/datasets and the cardiac cycle correspondence between the combined X-ray/fluoro datasets/images. The combined X-ray/fluoro and intravascular sensor images provided in the method for each position of intravascular measurement/slice along the blood vessel allows the physician the ability to determine the planned position of the treatment, e.g., a stent, in the X-ray/fluoro images based on the intravascular images, and allows an accurate assessment of the target/lesion location in the X-ray/fluoro images during treatment.

13 Claims, 4 Drawing Sheets

X-RAY/INTRAVASCULAR IMAGING COLOCATION METHOD AND SYSTEM

BACKGROUND OF INVENTION

The subject matter disclosed herein relates to the field of interventional cardiology, and more specifically to imaging techniques utilized in interventional cardiology procedures.

Interventional cardiology covers clinical procedures performed by physician for the sake of treating a coronary artery which is affected by a stenosis, i.e. a narrowing of the vessel. Due to this narrowing, blood supply to the heart/myocardium may be impacted. A common therapeutic option for this condition is to deploy a stent in the narrowed vessel. A stent is a metallic mesh structure which has a cylindrical form once deployed. This structure forces the vessel to return to a normal size due to the pressure exerted by the deployed stent and consequently the blood supply to the myocardium is hopefully restored.

This type of interventional cardiology procedure is done using a minimally invasive approach. In particular, the different interventional tools used in the procedure are guided or threaded to the place of interest in the artery/blood vessel under the guidance of images showing the structure and the surrounding tissue of the patient. The tools, normally in the form of a catheter, guidewire, and stent, are introduced at a puncture point, which could be the femoral artery or the radial artery. The images used by the physician to guide the catheter along the vessel to the desired/affected area are x-ray images which offer a field of view of several centimeters and depict all the anatomical elements which are inside this field of view. The contrast in these types of images depends on the x-ray absorption of the material by the x-rays. For example, the design/materials of the employed interventional tools makes them reasonably radio-opaque and easily visible in the x-ray images. For the anatomical tissue shown in the images, such as the vessel, this tissue can be more transparent making it potentially necessary to inject a contrast media to more readily visualize their structures in the patient.

In some cases, other imaging systems may be used as an alternative to x-ray images. The reasons for this can be that the physician may want to know some information on the vessel wall/structure to understand the root cause of the narrowing or to better define its extent within the vessel, which cannot be readily done with x-ray images. Indeed, it is common physiological knowledge that often the narrowing is due to a plaque which builds up on the vessel wall over time. The nature of this plaque may be variable, as it may be calcified, fibrous, etc. It is also known the first reaction of the vessel when a plaque starts to build up is to enlarge and thus attempt to maintain the lumen size. However, these details are not readily visible in x-ray image of the vessel, though they can be important in the treatment of the patient.

To address this issue, the industry has developed alternative and/or additional imaging modalities, such as Intra Vascular Ultra Sound (IVUS) or Optical Coherent Tomography (OCT). The general operation mode for these tools is to provide images from a signal obtained using a sensor navigated inside the artery itself. The images obtained from these modalities depict a slice of the tissue perpendicular to the longitudinal axis of the vessel. The location of this slice is precisely defined by the location of the sensor in the artery at the time when the signal was collected. In some other situations, a different sensor may be introduced in the artery such as a pressure sensor or a temperature sensor. In the cases using these types of sensors, the information collected is a single mono-dimensional signal, corresponding to the temporal variation of the signal collected by this sensor. In either configuration, the physician uses the images obtained using the sensors to position/reposition the catheter at the particular point of interest in the blood vessel for treatment.

The main steps of prior art interventional cardiac procedures employed using these known imaging techniques are the following:

Puncture the patient at the level of the femoral artery or radial artery,

Introduce a catheter and drive it under the guidance of x-ray images into the ostia of a coronary artery.

Perform some images of the coronary arteries with injection of contrast media.

Assuming that a stenosis area is revealed by these images and the physician decide that he wants to interrogate this vessel with intravascular imaging or intravascular sensor:

Introduce a guide wire inside the catheter and push it to the ostia of the coronary. Once the guide wire gets out of the catheter, the wire is navigated along the vessel to reach the distal portion of the diseased coronary artery.

Slide along the guide wire, which is used as rail, the intravascular equipment including the sensor. The appearance of this equipment in the x-ray image is usually a small elongated (2 or 3 mm length, ⅔ of mm diameter) object.

Activate the imaging/recording capability of the intravascular equipment.

Push/pull the intravascular equipment to observe at different locations along the vessel. Most times but not exclusively, the intravascular equipment is pulled using motorized pullback device acting at constant speed.

In parallel with the use of the sensor, the operator may at his discretion, obtain some x-ray images which display the position of the intravascular sensor inside the vessel.

Once the analysis of this data is finished, the physician can perform different actions such as deploying a stoat at the vessel section being identified as diseased, optimize the already deployed stent, etc.

The primary medical purpose associated with the use of intravascular device/equipment is to relate the information collected on the vessel via the intravascular equipment/sensor to a precise location along the image of the vessel obtained using the x-ray. In attempts to effectively achieve this, several prior art strategies exist:

(1) Use the physician's experience in analyzing both the x-ray image and the intravascular data to relate/correlate the information. For example, the physician may use the location of the narrowing illustrated in the two images and from this extrapolate the correspondence between the image and a location along the vessel. This approach is feasible when the intravascular data has been collected using a motorized pullback mechanism. Assuming a fixed acquisition rate, it is possible to roughly relate position in the vessel and position in the stack of intravascular data.

(2) Use advanced technical means (i.e., a computer modelling program) to build up an image of the vessel with a centerline that corresponds to the center of the vessel using the sensor data. This centerline is established in the 3D space and so any distance measured along it translates into a given difference of time assuming a constant speed for the automatic pullback of the sensor in the vessel. To relate the intravascular data with a given location, the operator can then manually define a common reference point. For example, he can point out a bifurcation of the vessel which can be observed in the two datasets.

(3) Use the following method steps:
Shoot x-ray (fluoroscopic low-dose) images while the probe is moved in the artery and the sensor images are obtained.
With an image processing algorithm, segment out the location of the probe in these images.
Report this position in a cine image done in the same configuration of, the x-ray imaging system. In reporting this position, the algorithm has to manage additional sources of errors such as cardiac motion and the breathing motion, as these two motions change the location of the vessel over time.

This third option presents a technical solution which is currently offered by some imaging manufacturers and is very attractive for use by physicians. However, it depends on reliable algorithms to perform the following analysis in the x-ray image:

Identification of a centerline for the vessels in the cine image,
Tracking of the location of the probe in the fluoroscopic images.

In performing the analysis, these algorithms must accurately account for significant errors that can occur as a result of the motion of the vessel in the images. Thus, the complexity of the analysis and accompanying algorithms and device is quite high in order to achieve an accurate correspondence between the various images.

In one other attempt to provide correlation between these types of images, it has been proposed in the prior art to add a localization sensor to the intravascular equipment. This localization sensor could then report the position of the probe along the vessel at any time. This information is provided in the same referential as the x-ray image of the vessel, and has the some of the same shortcomings with regard to the errors and algorithms required to overcome these errors for accurate images. With respect to the third option listed above, the challenging problem of tracking the location of the probe in the fluoroscopic images is avoided. On the other side from a technical complexity point of view, the inclusion of a localization sensor into the intravascular equipment is a significant difficulty. Moreover some other pieces of equipment shall be added to operate this sensor.

Hence it is desirable to provide a method and system for assessing a lesion or affected area of a blood vessel for treatment, including the nature of the lesion, the location of the lesion on the vascular tree, the dimension (e.g., length and diameter) of the lesion and tortuosity of the access to the lesion along the vascular tree that does not require complicated algorithms to correct for errors and/or fluctuations in the images obtained.

BRIEF DESCRIPTION OF THE INVENTION

There is a need or desire for a method and system that can provide images illustrating these attributes in an affected area of a blood vessel that does not include the above-mentioned drawbacks and needs in the prior art. These issues are addressed by the embodiments described herein in the following description of the invention, which is a method and system for producing a combined image of x-ray and intravascular sensor image.

In the method and associated system, a display provides a new sequence of combined X-ray/fluoro images obtained in synchrony with the intravascular dataset/images. This synchronization will be based on the time tags recorded at the acquisition of the X-ray/fluoroscopic and the intravascular images/datasets. The combined X-ray/fluoro and intravascular sensor images provided in the method for each position of intravascular measurement/slice along the blood vessel allows the physician the ability to determine the planned position of the treatment, e.g., the stent, in the X-ray/fluoro images based on the intravascular images, and allows an accurate assessment of the target/lesion location in the X-ray/fluoro images during treatment. In this method/process, the enhancement to the X-ray/fluoro images for each intravascular slice is performed in a synchronized review at any time immediately after acquisition of the images without any operator invention required, i.e., the method does not require any manual vessel segmentation, manual spatial registration or catheter detection/tracking in the performance of the analysis in the method. The method also is performed in a highly simplified manner without the need for complicated algorithms and/or additional pieces of equipment as required in the prior art.

One exemplary embodiment of the invention is a method for producing enhanced X-ray images of a blood vessel/myocardium, and a system for performing the method, including the steps of obtaining a first set of X-ray images of the blood vessel/myocardium over a single cardiac cycle, obtaining a second set of X-ray images of the blood vessel/myocardium over a number of cardiac cycles, synchronizing the second set of X-ray images and the first set of X-ray images with regard to the portion of the cardiac cycle at which each image was obtained and overlaying one of the first set of X-ray images with a synchronized one of the second set of X-ray images to produce a combined X-ray image.

Another exemplary embodiment of the invention is a method for producing enhanced X-ray images of a blood vessel/myocardium, and a system for performing the method, including the steps of obtaining a first set of X-ray images of the blood vessel/myocardium over a single cardiac cycle, obtaining a second set of X-ray images of the blood vessel/myocardium over a number of cardiac cycles, obtaining a set of intravascular images of the blood vessel/myocardium concurrently with obtaining the second set of X-ray images; synchronizing the set of intravascular images and the second set of X-ray images with regard to the time each of the set of intravascular images and each of the second set of X-ray images was obtained and overlaying one of the first set of X-ray images with a corresponding one of the second set of X-ray images to produce a combined X-ray image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention relate to a method for displaying synchronized X-ray/fluoro images obtained with and without simultaneous intravascular imaging in order to readily locate and display the position of a catheter utilized in the intravascular imaging within the X-ray/fluoro images.

Figure 1:
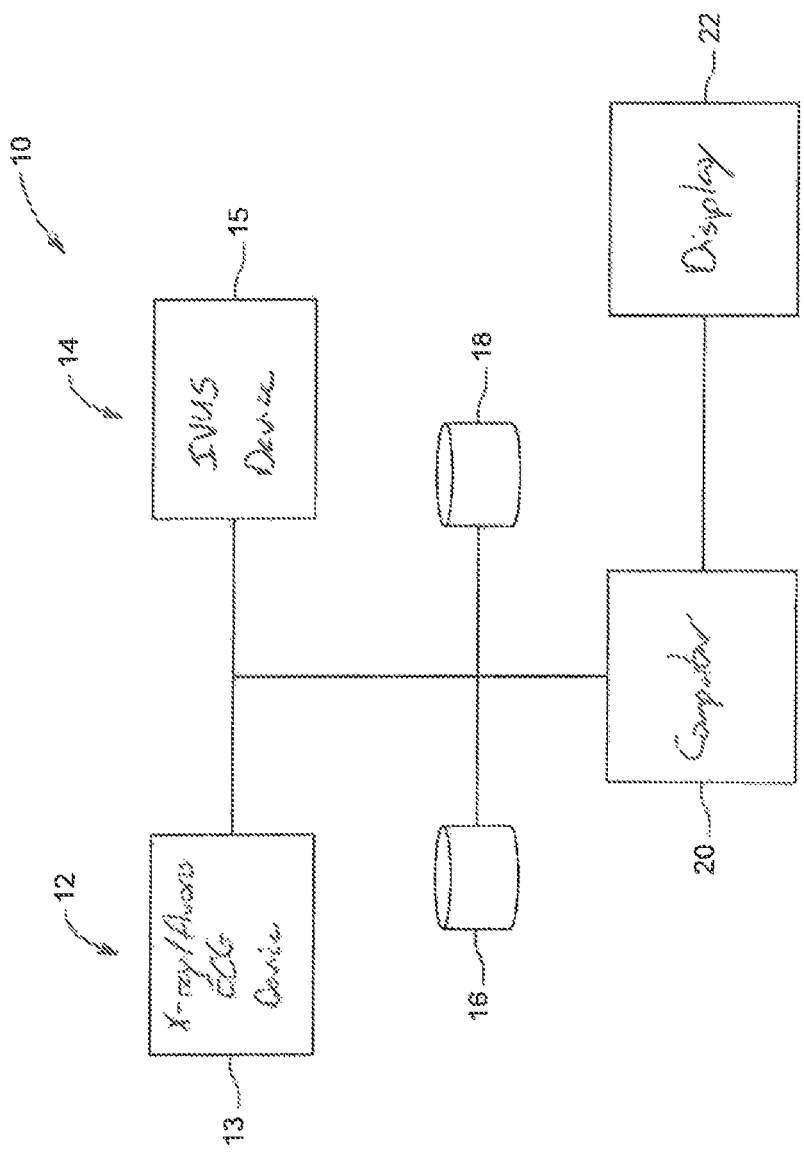
FIG. 1 is a block diagram of an multimodal imaging system according to one exemplary embodiment of the invention.

In the exemplary embodiment of the invention illustrated in FIG. 1, a multimodal imaging system 10 is shown that includes an X-ray/fluoro imaging system 12 and an intravascular imaging system 14. The systems 12 and 14 can be any suitable imaging systems, with one example for the X-ray/fluoro system 12 being an angiographic or X-ray/fluoro/ECG device 13, which can also be separate X-ray/fluoro and ECG devices, such as the IGS 520 sold by GE Healthcare, and one example of the intravascular imaging system 14 being and intravascular ultrasound (IVUS) device 15, such as those manufactured and sold by Volcano under the name Eagle Eye IVUS, by Acist under the name HD IVUS or by Boston Scientific under the name Opticross Coronary Imaging catheter As shown in FIG. 1, the X-ray/fluoro/ECG device 13 is operably connected to a database 16 within which the X-ray/fluoro datasets or images 24, 28 and ECG recordings 17,27 (FIGS. 2 and 3) are stored, and the IVUS device 15 is operably connected to a database 18 in which the IVUS images 30 (FIGS. 3 and 4) are stored. Each of the databases 16 and 18 is further operably connected to a suitable computer or processing unit 20, which is also optionally operably connected to the devices 12,13 and 14,15, and to a display 22 for displaying the various images 24, 28 and 30, which can be formed on or separate from the devices 12,13 and 14,15.

Figure 2:
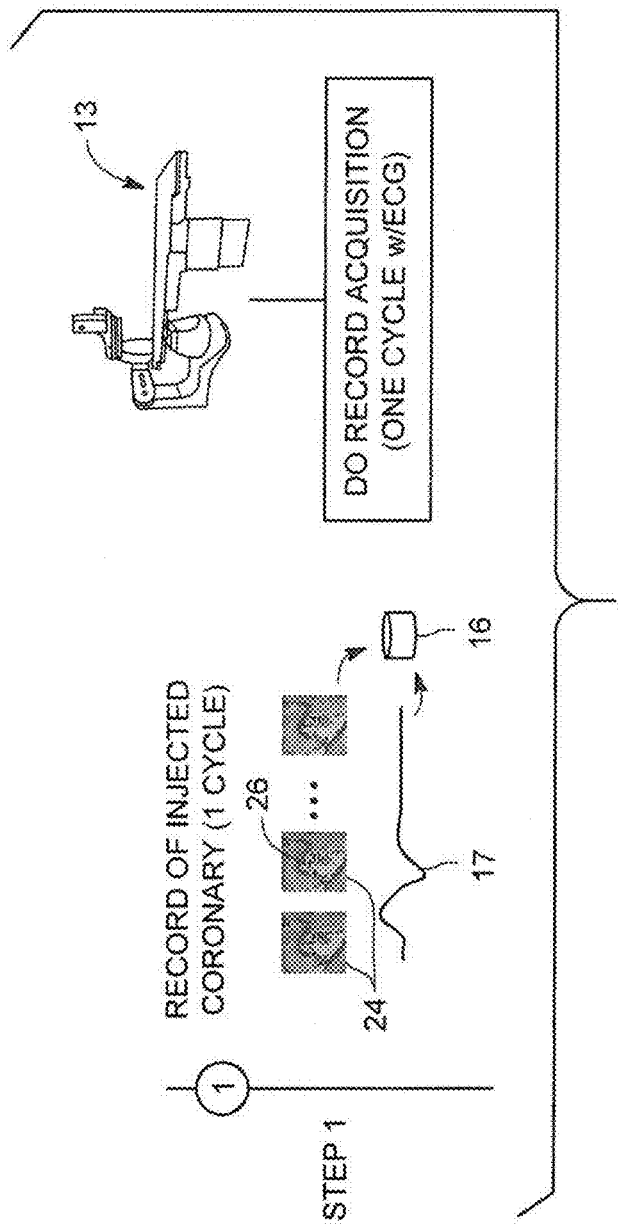
FIG. 2 is a schematic view of an X-ray/fluoro imaging system of the imaging system and associated recorded cardiac cycle images obtained by the X-ray/fluoro imaging system operated according to a first step of an exemplary embodiment of the invention.
Figure 3:
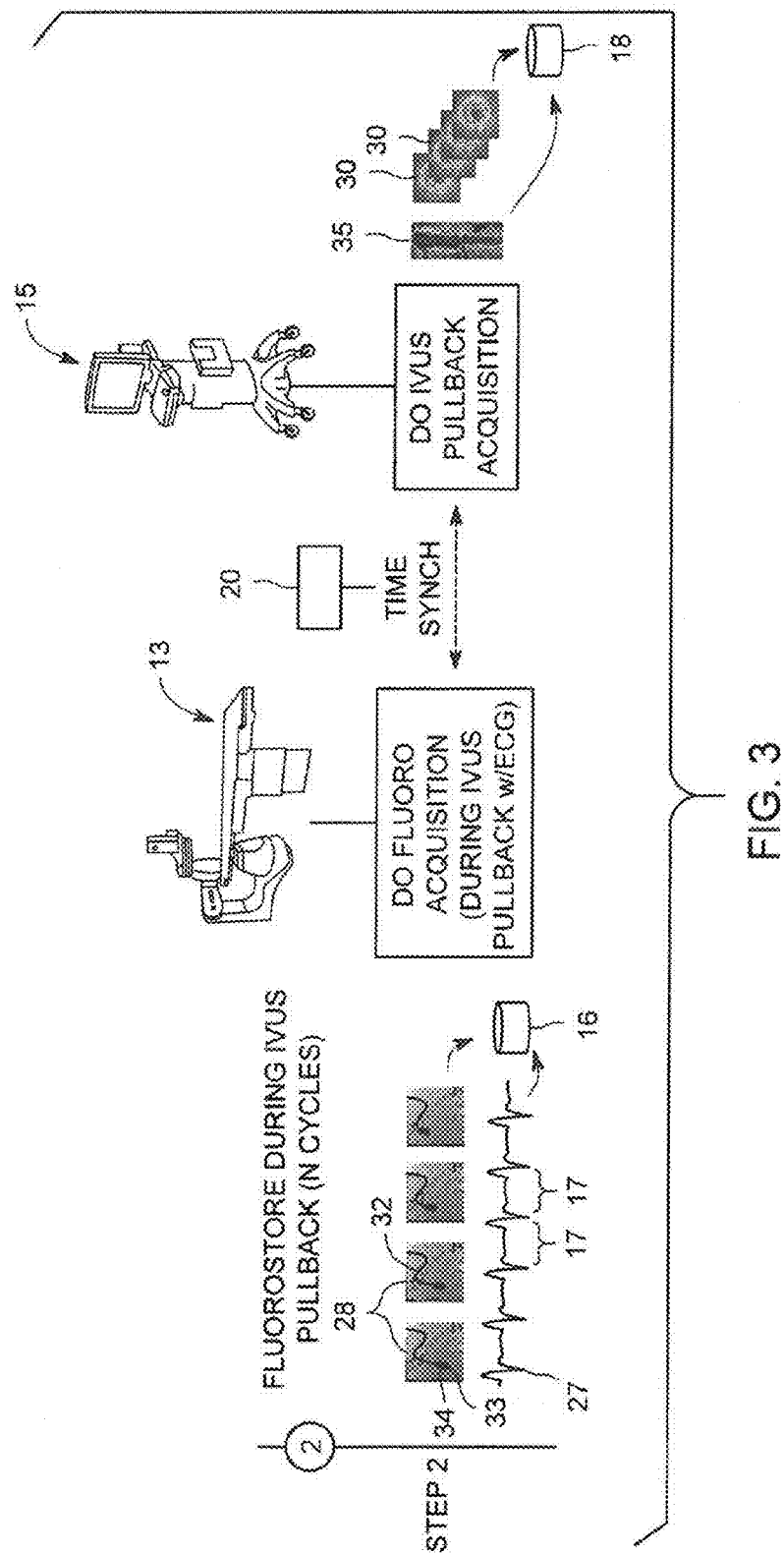
FIG. 3 is a schematic view of an X-ray/fluoro imaging system and associated recorded cardiac cycle images obtained by the X-ray/fluoro imaging system and an intravascular imaging system and associated intravascular images obtained by the intravascular imaging system operated according to a second step of an exemplary embodiment of the invention.
Figure 4:
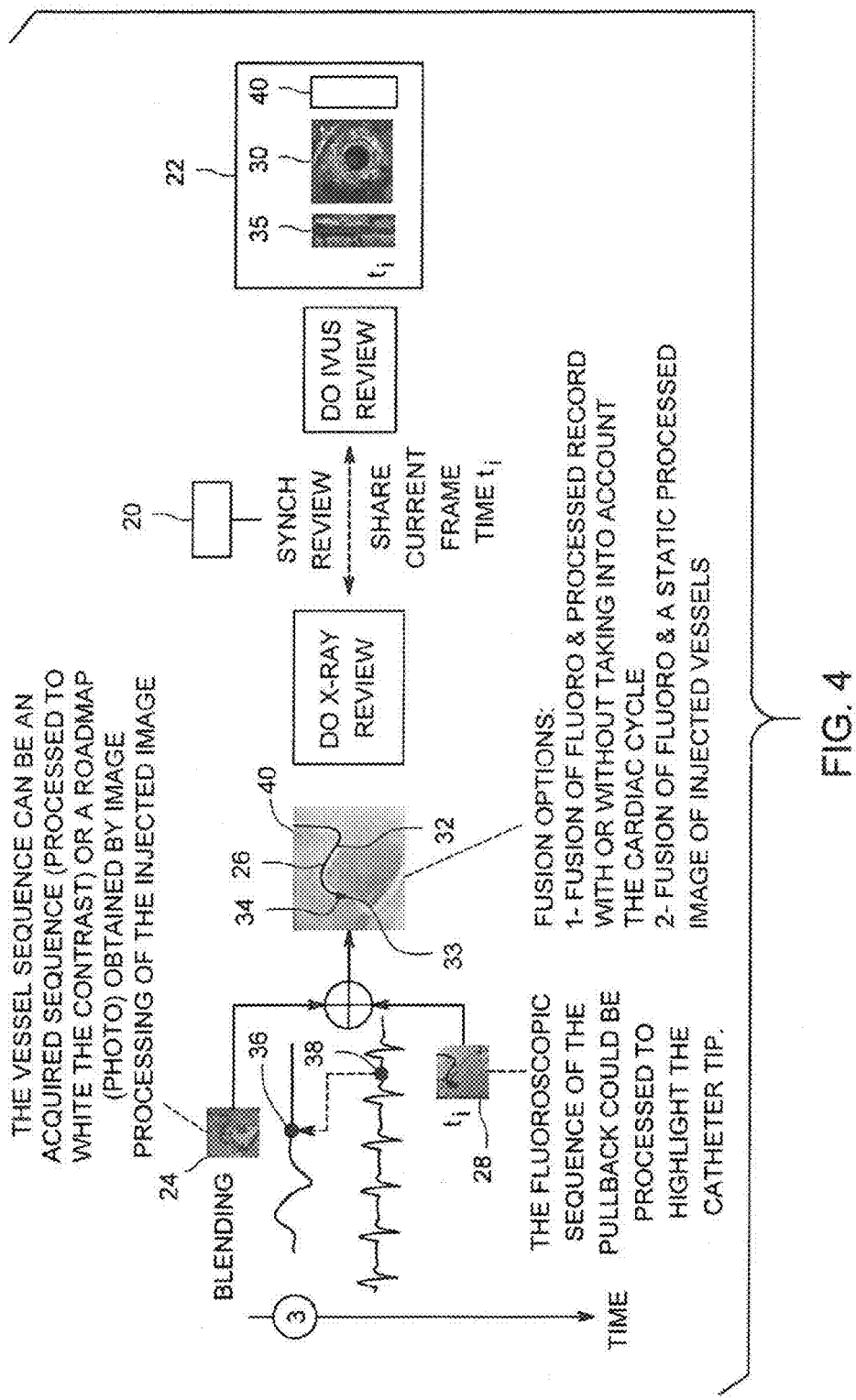
FIG. 4 is a schematic view of the combination of recorded cardiac cycle images obtained by the X-ray/fluoro imaging system and intravascular images obtained by the intravascular imaging system operated according to a third step of an exemplary embodiment of the invention.

Looking now at FIGS. 2-4, the method includes a sequence of image acquisition steps that utilizes the X-ray/fluoro/ECG device 13 in Step 1. In Step 1, as illustrated in FIG. 2, the X-ray/fluoro/ECG device 13 is used to perform a record or segmented acquisition of a first set of X-ray/fluoro images 24 over an ECG recording of a single cardiac cycle 17, i.e., a first recorded ECG signal, of the patient (not shown), such as in an Acquisition Mode for the device 13. The sequence of the images 24 over the cardiac cycle 17 in this step are obtained after the injection of a contrast agent into the patient in order to more clearly illustrate the structure of the blood vessels/myocardium 26 represented within the images 24. In addition, as these images 24 are obtained, they are identified/tagged by the time or position within the cardiac cycle 17 in which they were obtained and stored within the database 16. The process used in this initial step to identify the images 24 is similar to the process utilized in producing cine or movie images of the blood vessels/myocardium 26 by using known ECG tracing techniques to take the images 24 at different stages of the ECG recorded cardiac cycle 17, which may then be looped in order to illustrate the motion of the blood vessels/myocardium 26 over the recorded cycle 17 to identify any issues from the images 24. The segmented acquisition sequence of the images 24 taken in this step can be enhanced as desired using the device 13 and/or the computer 20 connected to the database 16, such as into an acquired sequence, where the images 24 are processed to white the contrast that was injected, or a roadmap/photo obtained by processing of the individual images 24 of the injected. Further, the computer 20 can identify the X-ray/fluoro images 24 as the overlay images to be utilized in the following steps of the overall method.

Referring now to FIG. 3, after the X-ray/fluoro images 24 have been obtained and stored, in Step 2 the X-ray/fluoro/ECG device 13 is utilized to obtain a second set of X-ray/fluoro images 28 of the blood vessels/myocardium 26 over a number N of ECG recorded cardiac cycles 27, i.e., a second recorded ECG signal, where N>1, such as in a FluoroStore mode for the device 13. These X-ray/fluoro images 28 are stored in database 16, or alternatively in a separate database (not shown) and are taken without any injected contrast agent present in the blood vessels/myocardium 26 such that the location of an intravascular catheter 32 operably connected to the IVUS device 15 within the blood vessels/myocardium 26 can be shown in the X-ray/fluoro images 28. However, with the lack of contrast agent, the structure of the blood vessel/myocardium 26 is not shown at all in the X-ray/fluoro images 28.

Concurrently, a set of IVUS images 30 are obtained of the blood vessel/myocardium 26 using the IVUS device 15 during the pullback of the intravascular catheter 32 including a sensor 33 at a catheter tip 34, that is positioned within the blood vessels/myocardium 26 and connected to the IVUS device 15. The images 30 illustrate slices of the blood vessel/myocardium 26 that are oriented perpendicular to the catheter tip 34. The pullback of the IVUS catheter 32 provides individual slices/images 30 of the blood vessels/myocardium 26 at each point along the blood vessels/myocardium 26 where the images 30 are obtained. Also, these slices/images 30 from the sensor 33 can be stacked/combined by the computer 20 to form a three-dimensional representation/roadmap image 35 of the blood vessel/myocardium 26, as shown in FIGS. 3 and 4, which can be shown along with the selected slice(s) 30.

Over the time period of Step 2 in which the second set of X-ray/fluoro images 28 and the set of IVUS images 30 are obtained, the images 28,30 are linked or time tagged/synced with one another as they are obtained in a known manner, such as by using the computer 20 or other suitable device(s) (not shown) in order to provide a registration between the images 28,30 that are taken at the same time during this step of the method. In addition, as they are obtained, the images 28,30 are subsequently stored within the databases 16,18 associated with the respective devices 13,15 that obtained the images 28,30. Further, the second set of X-ray/fluoro images 28 is also recorded within the database 16 with an identification of the segment/portion of the individual cardiac cycle 17 within the sequence of cycles 27 at which each particular image 28 was obtained, in order to enable the computer 20 to relate the images 28 to an image 24 taken of the blood vessel/myocardium 26 over the single cycle 17 that is identical or at least closely related in time to the segment/portion of the cycle 17 at which the image 28 was taken.

Referring now to FIG. 4, with the X-ray/fluoro images 24,28 of the blood vessels/myocardium 26 stored and synced with the portions of the ECG recorded cardiac cycle 17 at which they were obtained, and the X-ray/fluoro images 28 additionally synced with the IVUS images 30 based on the acquisition time $t_i$ at which they were obtained, the computer 20 can conduct an analysis of the images 24,28,30 in order to provide a combined X-ray/fluoro image 40 on the display 22 in association with a selected IVUS image/slice 30 in Step 3. This combined image 40 is a combination of the X-ray/fluoro image 28 taken at the acquisition time $t_i$ corresponding to each IVUS image/slice 30 and the X-ray/fluoro image 24 taken at the point of the ECG recorded cardiac cycle 17 closest in time to the point in the ECG recorded cycle 17 in the sequence of cycles 27 at which the X-ray/fluoro image 28 was obtained.

In performing the analysis on and blending of the images 24,28,30 to produce the combined images 32 in Step 3, when the physician initiates a review of the images 24,28,30 by selecting a particular slice or IVUS image 30 for review, the computer 22 determines the acquisition time $t_i$ during Step 2 at which the selected image 30 was obtained, as stored in conjunction with the selected slice 30 in database 18. As a result of the time sync/registration performed by the computer 20 for the X-ray/fluoro images 28 and IVUS images 30 obtained in Step 2, the computer 20 can locate the particular X-ray/fluoro image 28 in the database 16 obtained at the same acquisition time $t_i$ of Step 2 for the selected IVUS slice 30.

In addition, once the X-ray/fluoro image 28 associated with the selected IVUS image 30 has been determined using the time synchronization/registration between the images 28,30, in Step 3 the computer 20 can additionally determine the point 36 in the particular ECG recorded cardiac cycle 17 of the sequence of cycles 27 covered in Step 2 at which the X-ray/fluoro image 28 was obtained. This can be one using the acquisition time $t_i$ and locating the particular cycle 17 and point 36 within that cycle 17 corresponding to the acquisition time $t_i$. The computer 20 then locates the X-ray/fluoro image 24 taken at the point 38 of the ECG recorded single cycle 17 covered in Step 1 corresponding as closely in time as possible to the point of the cycle 17 at which the X-ray/fluoro image 28 was obtained.

Once the X-ray/fluoro images 24 and 28 are located that correspond with regard to one another based on the points 36,38 of the individual ECG recorded cardiac cycles 17 in Step 1 and Step 2, the X-ray/fluoro images 24,28 can be overlaid on one another on the display 22, or in any other suitable manner, by the computer 20 in Step 3. IN a specific exemplary embodiment, the process performed in Step 3 to combine the X-ray images 24 and 28 is performed without any algorithms required in the prior art to accommodate for the significant errors that can occur as a result of the motion of the vessel in the images. In doing so, the contrast defining the structure of the blood vessels/myocardium 26 provided by the agent injected for the image 24 is superimposed on the image 28 illustrating/highlighting the position of the tip 34 of the IVUS catheter 32 on the display 22. Thus, the combined image 40 formed by overlaying X-ray/fluoro image 24 on X-ray/fluoro image 28, or vice versa, provides both a clear view of the structure of the blood vessels/myocardium 26 and the position of the catheter tip 34 and catheter 32 within the blood vessels/myocardium 26. In doing so, the computer 20 can additionally process the image 40 to enhance the representation of the catheter tip 34 in the combined image 40, while also clearly illustrating the vessel 26 from the injected image 24 of Step 1.

After the analysis and processing has been completed, the combined image 32 can be presented along with the selected IVUS image 30 to provide additional information to the physician regarding the internal structures of the blood vessels/myocardium 26. The different images provided on the display 22, namely the IVUS image/slice 30, the stacked slices/roadmap 35 and the combined X-ray/fluoro image 40, thus enable the physician to assess the position of the intravascular probe with respect to the vessel. Further, the array if images 30,35,40 allow the physician to better assess the target-lesion location within the blood vessels/myocardium 26 and to display the planned location of placement for the stent used to treat the lesion.

In other exemplary embodiments of the invention, in processing/combining the X-ray/fluoro images 24,28 from Steps 1 and 2 to form the combined image 40, with or without inclusion of any corresponding IVUS images 30, there are different optional processes that may be used to enhance the image 40 as presented, which are as follows:

Process the X-ray/fluoro image 28 to make the probe more visible in this image 28. This processing can take the form of, for example, displaying the image in an inverted video, or applying an image processing filter to the image 28 that enhances curvilinear structures. Another strategy may be to use color within the images 24,28 and represent the X-ray/fluoro images 24,28 along different color ramps.

Distort the X-ray/fluoro image 28 in a known manner to compensate for motion induced by the respiration of the patient.

One record frame/image 24 from Step 1 (with or without ECG recordal for registration purposes) can be combined/fused with the all of the X-ray/fluoro images 28 from Step 2 (taken with or without ECG recordal for registration purposes).

The entire set of X-ray images 24 from Step 1 (with ECG recordal for registration purposes) can be combined with the entire set of X-ray/fluoro images 28 obtained in Step 2 with ECG recordal for registration purposes.

In still another exemplary embodiment of the invention, the X-ray/fluoro images 24 from Step 1 can be combined in Step 3 to form a small video loop covering the cardiac cycle 17. The different X-ray/fluoro images 28 taken in Step 2 are then combined with the corresponding image 24 from Step 1 based on the ECG recordal of the cardiac cycles 17,27 corresponding to the images 24,28 for registration purposes. After combination of the images 28 with the corresponding images 24 in the video, the video can be looped to cover the sequence 27 of multiple cardiac cycles 17 covered within the images 28 obtained in Step 2. In this method, the correspondence between the images 24,28 of Step 1 and Step 2 is defined by considering the images 24 and 28 which are the closest in time during their respective cardiac cycles 17. The position in the cardiac cycle 17 is commonly identified by analyzing the ECG tracings based on well-known algorithms and/or ECG triggered segmented imaging, which can be used to correlate the individual images 24 and 28 with one another.

In still other exemplary embodiments of the invention, it is contemplated that the combined X-ray/fluoro images 40 can be utilized in conjunction with other intravascular imaging modalities/devices 14, such as OCT, and/or with other intravascular sensors 33, such as a blood pressure sensor. Additionally, the images 28 of Step 2 can be obtained with contrast material injected into the blood vessels/myocardium 26 with additional features present in the system 10 in order to effectively highlight the catheter tip 34 in the resulting X-ray/fluoro images 28 taken during the pullback of the sensor 33/tip 34 in Step 2. In one exemplary embodiment of this variation, a navigation system (not shown) with an antenna/sensor 33 in the catheter tip 34 can be utilized to identify the position of the tip 34 in the images 28 and the combined images 40. Also, to reduce the dosage during the image acquisitions, the frame rate for the X-ray/fluoro images 28 may be very low with collimation during the sensor pullback acquisitions.

To perform the above exemplary embodiments of the method, any suitable system 10 can be utilized that is similar to those discussed previously. In addition, the method can be performed on the system 10 by integrate all the elements/functions of the method in a single software application hosted on suitable imaging equipment such as, for example, an angiographic unit 12,13. The method can additionally be performed utilizing an open interface (not shown) between the respective imaging devices 12, 14 utilized in the system 10.

In still another alternative exemplary embodiment for the implementation of the method, the method can be compiled as an application capable of being stored on and performed or run by the angiographic unit 12,13 to produce the combined X-ray image(s) 40. Correspondingly, a protocol that is openly available on the network (not shown) to which the devices 12,14 are operably connected can be utilized to indicate in conjunction with the display of the image 40 the time tag of the currently displayed combined image 40. This time tag can then be used by the intravascular equipment/device 14 to display the information/image 32 that was collected at this time tag. Additionally, the protocol can be used in reverse as well, with a display of the proper combined x-ray image 40 resulting from the time tag provided to the angiographic unit 12,13 by the intravascular equipment 14.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for producing enhanced X-ray images of a blood vessel/myocardium, the method comprising the steps of:
   obtaining a first set of X-ray images of the blood vessel/myocardium over a single cardiac cycle;
   recording a first ECG signal for the single cardiac cycle concurrently with obtaining the first set of X-ray images;
   obtaining a second set of X-ray images of the blood vessel/myocardium over a number of cardiac cycles;
   recording a second ECG signal for the number of cardiac cycles concurrently with obtaining the second set of X-ray images;
   obtaining a set of intravascular images of the blood vessel/myocardium concurrently with obtaining the second set of X-ray images;
   synchronizing the set of intravascular images and the second set of X-ray images with regard to the time each of the set of intravascular images and each of the second set of X-ray images was obtained;
   selecting one of the set of intravascular images for review after obtaining the set of intravascular images;
   reviewing the second set of X-ray images to determine the one of the second set of X-ray images obtained at the same time as the selected one of the set of intravascular images;
   reviewing the first ECG signal to determine a first point in the single cardiac cycle at which one of the first set of X-ray images was obtained;
   reviewing the second ECG signal to determine a second point within the number of cardiac cycles that the one of the second set of X-ray images obtained at the same time as the selected one of the set of intravascular images was obtained, wherein the second point closely corresponds to the first point in their respective positions within the respective cardiac cycles; and
   overlaying the one of the first set of X-ray images taken at the first point with the one of the second set of X-ray images taken at the second point to form the combined X-ray image.

2. The method of claim 1, wherein the step of overlaying the one of the first set of X-ray images with the one of the second set of X-ray images comprises processing at least one of the one of the first set of X-ray images or the one of the second set of X-ray images.

3. The method of claim 2, wherein the step of processing at least one of the one of the first set of X-ray images or the one of the second set of X-ray images comprises applying an image processing filter to the one of the second set of X-ray images that enhances curvilinear structures.

4. The method of claim 2, wherein the step of processing at least one of the one of the first set of X-ray images or the one of the second set of X-ray images comprises distorting the one of the second set of X-ray images in a known manner to compensate for motion of the blood vessels/myocardium induced by respiration.

5. The method of claim 2, wherein the step of processing at least one of the one of the first set of X-ray images or the one of the second set of X-ray images comprises the steps of:
   combining the first set of X-ray images to form a small video loop covering the single cardiac cycle; and
   overlaying each of the second set of X-ray images with the one of the first set of X-ray images corresponding to their respective positions within the respective cardiac cycles to form a video of the sequence of multiple cardiac cycles covered by the second set of X-ray images.

6. The method of claim 1, wherein the step overlaying the one of the first set of X-ray images taken at the first point with the one of the second set of X-ray images taken at the second point comprises overlaying the entire first set of X-ray images with the entire second set of X-ray images.

7. The method of claim 1 further comprising the step of displaying the combined X-ray image in conjunction with the selected one of the set of intravascular images.

8. The method of claim 7 wherein the step of displaying the combined X-ray image in conjunction with the selected one of the set of intravascular images comprises displaying the combined X-ray image, the selected one of the set of intravascular images and a stacked roadmap image combining all of the set of intravascular images.

9. The method of claim 1, wherein the step overlaying the one of the first set of X-ray images taken at the first point with the one of the second set of X-ray images taken at the second point comprises overlaying the one of the first set of X-ray images taken at the first point with each of the second set of X-ray images to form a number of combined X-ray images.

10. A method for producing enhanced X-ray images of a blood vessel/myocardium, the method comprising the steps of:
   obtaining a first set of X-ray images of the blood vessel/myocardium over a single cardiac cycle;
   obtaining a second set of X-ray images of the blood vessel/myocardium over a number of cardiac cycles;
   synchronizing the second set of X-ray images and the first set of X-ray images with regard to the portion of the cardiac cycle at which each image was obtained; and
   overlaying one of the first set of X-ray images with each of the second set of X-ray images to form a number of combined X-ray images on a display.

11. The method of claim 10 further comprising the step of injecting a contrast agent into the blood vessel/myocardium prior to obtaining the first set of X-ray images.

12. An imaging system for performing a method for producing enhanced X-ray images of a blood vessel/myocardium, the method comprising the steps of:
   obtaining a first set of X-ray images of the blood vessel/myocardium over a single cardiac cycle;
   obtaining a second set of X-ray images of the blood vessel/myocardium over a number of cardiac cycles;
   obtaining a set of intravascular images of the blood vessel/myocardium concurrently with obtaining the second set of X-ray images;
   synchronizing the set of intravascular images and the second set of X-ray images with regard to the time each of the set of intravascular images and each of the second set of X-ray images was obtained;
   overlaying one of the first set of X-ray images with each of the second set of X-ray images to produce combined X-ray images on a display;
   selecting one of the set of intravascular images for review after obtaining the set of intravascular images; and
   reviewing the second set of X-ray images to determine the one of the second set of X-ray images obtained at the same time as the selected one of the set of intravascular images.

13. The imaging system of claim 12, wherein said system:
   records a first ECG signal for the single cardiac cycle concurrently with obtaining the first set of X-ray images; and
   records a second ECG signal for the number of cardiac cycles concurrently with obtaining the second set of X-ray images.

* * * * *